United States Patent [19]

Rowan et al.

[11] Patent Number: 4,889,647

[45] Date of Patent: Dec. 26, 1989

[54] ORGANIC MOLYBDENUM COMPLEXES

[75] Inventors: Eugene V. Rowan, Rowayton; Thomas J. Karol, Norwalk; Homer H. Farmer, Westport, all of Conn.

[73] Assignee: R. T. Vanderbilt Company, Inc., Norwalk, Conn.

[21] Appl. No.: 797,732

[22] Filed: Nov. 14, 1985

[51] Int. Cl.$^4$ .......................................... C10M 133/16
[52] U.S. Cl. .................................. 252/42.7; 556/57; 556/61; 556/63
[58] Field of Search ................ 252/42.7, 46.6; 556/57, 556/61, 63

[56] References Cited

U.S. PATENT DOCUMENTS

| | | | |
|---|---|---|---|
| 2,795,552 | 6/1957 | Abbott et al. | 252/49.7 |
| 2,805,997 | 9/1957 | Benoit et al. | 252/42.7 |
| 3,184,410 | 5/1965 | Bretherick | 252/42.7 |
| 3,285,942 | 11/1966 | Price et al. | 260/429 |
| 3,349,108 | 10/1967 | Marzluff | 556/57 |
| 3,356,702 | 12/1967 | Farmer et al. | 252/42.7 |
| 4,009,122 | 2/1977 | Lines et al. | 252/431 N |
| 4,164,473 | 8/1979 | Coupland et al. | 252/42.7 |
| 4,217,292 | 8/1980 | Kroenke | 556/57 |
| 4,259,254 | 3/1981 | Bridger | 260/429 R |
| 4,474,674 | 10/1984 | Gutierrez et al. | 556/57 |

FOREIGN PATENT DOCUMENTS 659775  3/1963  Canada ............................. 252/42.7

Primary Examiner—Mark L. Bell
Assistant Examiner—Ellen McAvoy
Attorney, Agent, or Firm—Rasma B. Balodis

[57] ABSTRACT

New molbdenum complexes prepared by reacting (a) a fatty oil, (b) diethanolamine and (c) a molybdenum source are described. The molybdenum complexes impart antifriction and antiwear properties to lubricating compositions and decrease fuel consumption in internal combustion engine using same.

4 Claims, 1 Drawing Sheet

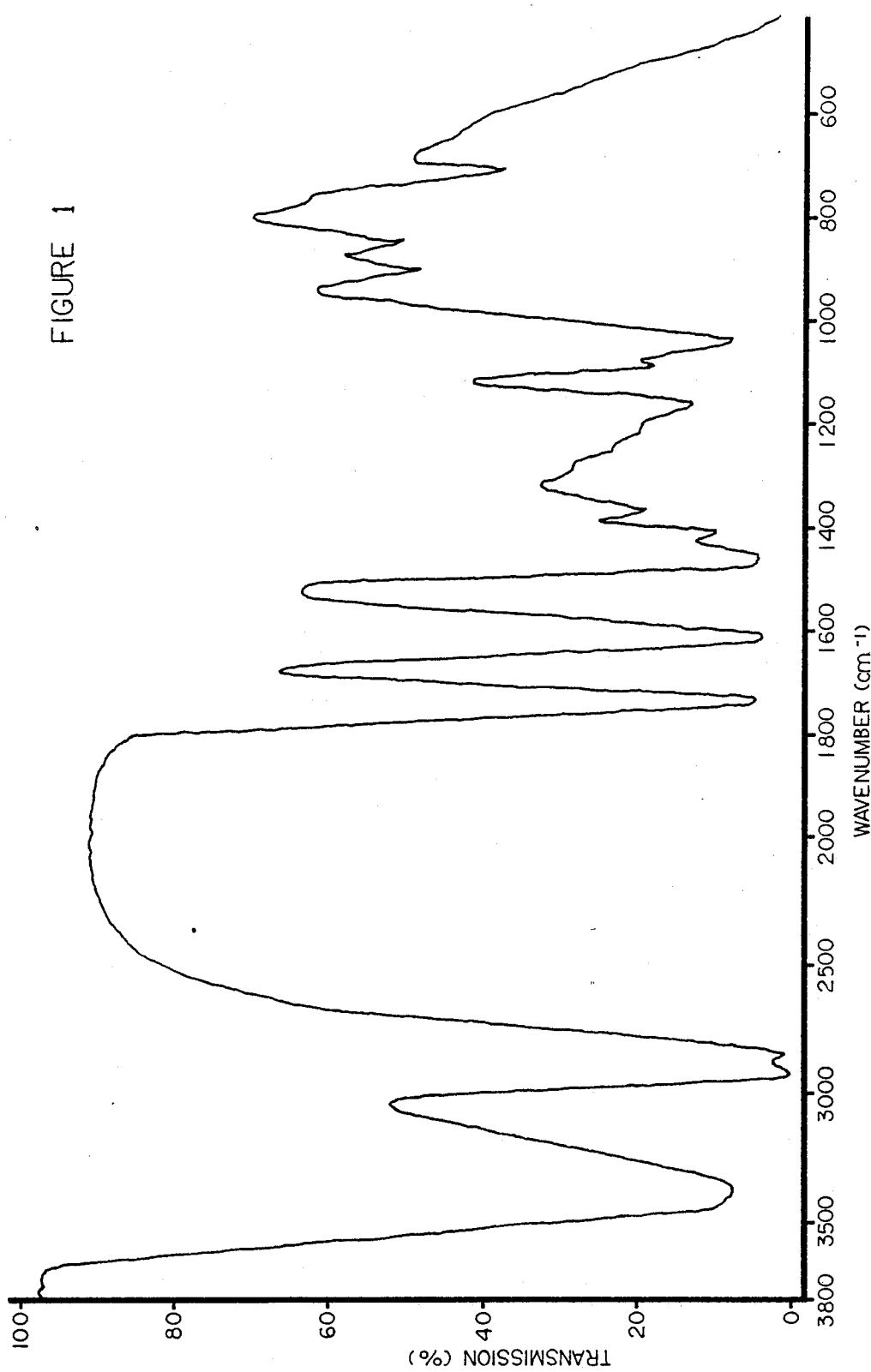

ORGANIC MOLYBDENUM COMPLEXES

BACKGROUND OF THE INVENTION

The present invention concerns novel organic molybdenum complexes and their use as friction and wear reducing additives for lubricating compositions. It further relates to a method of reducing fuel consumption in internal combustion engines by adding the new complexes to the lubricants used therein.

Many attempts to reduce fuel consumption in engines have been of mechanical nature. Another approach to the problem is the use of lubricants that reduce the internal friction in the engine thus resulting in a reduction in the engine's energy requirements. Friction is of particular significance in internal combustion engines, because loss of substantial amount of theoretical mileage is traceable directly to friction. Friction will increase the power required to effect movement, thus increasing fuel consumption. Therefore, it is advantageous to use lubricants which minimize this friction.

Since various antifriction additives act in a different physical or chemical manner, only some satisfy the effectiveness and compatibility criteria leading to a significant energy loss prevention function of the lubricant. Types of molybdenum compounds known to be useful in engine lubricants include certain dithiocarbamate derivatives of molybdenum disclosed in U.S. Pat. No. 4,259,254. The use of molybdenum complexes of fatty alkyl amines in conjuction with a sulfur donor is taught in U.S. Pat. No. 4,164,473.

It has been now discovered that a novel class of organomolybdenum complexes imparts both antifriction and antiwear properties to lubricants resulting in increased energy efficiency.

SUMMARY OF THE INVENTION

In accordance with the present invention, there are provided molybdenum complexes prepared by reacting (a) about 1 mole fatty oil, (b) about 1.0 to 2.5 moles diethanolamine and (c) a molybdenum source sufficient to yield about 0.1 to 6.0 percent of molybdenum based on the weight of the complex.

Another object of the invention concerns lubricating compositions comprising a major portion of a lubricating oil and a friction reducing amount of said molybdenum complex.

DETAILED DESCRIPTION OF THE INVENTION

The molybdenum complexes of the invention are reaction products of a fatty oil, diethanolamine and a molybdenum source. A specific chemical structure cannot be assigned to the product. It is believed that some of the components may have the structural formulae

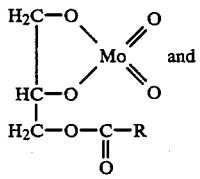

and $$R-\overset{O}{\underset{\|}{C}}-N\begin{matrix}CH_2-CH_2-O\\ \\CH_2-CH_2-O\end{matrix}\begin{matrix}\diagdown\\Mo\\\diagup\end{matrix}\begin{matrix}\diagup O\\ \\\diagdown O\end{matrix}$$

wherein R represents a fatty oily residue.

FIG. 1 of the drawing illustrates the infrared spectrum of a typical reaction product of the invention wherein the fatty oil residue is derived from coconut oil. The product is characterized by the infrared spectrum having an ester carbonyl band at 1740 cm$^{-1}$ and an amide carbonyl band at 1620 cm$^{-1}$.

The fatty oils are glyceryl esters of higher fatty acids containing at least 12 carbon atoms and may contain 22 carbon atoms and higher. Such esters are commonly known as vegetable and animal oils. Vegetable oils particularly useful are oils derived from coconut, corn, cottonseed, linseed, peanut, soybean, and sunflower seed. Similarly, animaly fatty oils such as tallow may be used.

The source of molybdenum is an oxygen-containing molybdenum compound capable of reacting with the reaction product of fatty oil and diethanolamine to form an ester-type molybdenum complex. The sources of molybdenum include, among others, ammonium molybdates, molybdenum oxides and mixtures thereof.

The reaction products are prepared by a condensation reaction. Generally, about 1.0 to 2.5, preferably 1.0 to 2.0 moles of diethanolamine are used per mole of fatty oil. If excess oil is used, the unreacted portion will act as a diluent for the product and the entire mixture may be incorporated into the lubricating composition.

The molybdenum source is added in a sufficient quantity to yield 0.1 to 6.0, preferably 0.5 to 2.0, optimally 1.0 to 1.25 percent of molybdenum per total product.

The reaction is conducted at elevated temperatures to accelerate said reaction and remove water of reaction. For example, temperatures of about 70° C. to 160° C. may be used depending upon the particular reactants.

The amount of the molybdenum complex in the lubricating composition may range from about 0.01 to 6.0 percent and preferably, from about 0.1 to 1.0 percent. An amount of 0.01 percent of the molybdenum complex is the minimum effective amount for imparting friction reducing properties to lubricating compositions. Amounts over 1 percent do not appreciably enhance antifriction properties, but will enhance antiwear properties. Amounts over 6 percent are not cost effective.

The lubricating compositions contemplated herein include lubricating oils containing a major amount of base oil. The base oil may be selected from oils derived from petroleum hydrocarbon and synthetic sources. The hydrocarbon base oil may be selected from napthenic, aromatic and paraffinic mineral oils. The synthetic oils may be selected from, among others, alkylene polymers, polysiloxanes, carboxylic acid esters and polyglycol ethers.

The lubricating compositions may contain the necessary ingredients to prepare the composition as for example dispersing agents, emulsifiers and viscosity improvers. Depending on the intended use of the lubricant, other functional additives may be added to enhance a particular property of the lubricant. The lubricating compositions may further contain known antioxidants, extreme pressure agents, metal passivators, rust inhibitors and other antiwear agents.

The following examples are given for the purpose of further illustrating the invention. All percentages and parts are based on weight unless otherwise indicated.

EXAMPLE I

A reactor was charged with 310 parts (0.47 moles) of coconut oil and 90 parts (0.86 moles) of diethanolamine and reacted for 2.5 hours at 135° to 140° C. Then 18.5 parts of 50% aqueous solution of ammonium heptamobybdate (0.053 moles Mo) were added to the reaction mixture and heated for 1.5 hours at 105° to 111° C. with removal of water under vacuum. After cooling, the solution was filtered. The light amber liquid had a molybdenum content of 1.0 percent and an infrared spectrum illustrated in FIG. 1.

EXAMPLE II

A reactor was charged with 310 parts (0.47 moles) of coconut oil and 90 parts (0.86 moles) of diethanolamine and reacted for 2.5 hours at 135° to 140° C. Then 0.0476 moles molybdenum were added in the form of aqueous solution of 6.6 parts molybdenum trioxide, 0.33 parts ammonium heptamolybdate and 52.6 parts water. The reaction mixture was heated for 1.5 hours at 105° to 110° C. with removal of water under vacuum. After cooling, the solution was filtered. The light amber liquid had a molybdenum content of 1.19 percent.

EXAMPLE III

A reactor was charged with 115.2 g (0.133 moles) of cottonseed oil and 24.8 g (0.240 moles) of diethanolamine. The reaction was blanketed with nitrogen and heated with stirring for three hours at 135° to 140° C. Then 22 g molybdenum trioxide was added, followed by a solvent system consisting of 150 g toluene, 25 g dimethylformamide and 100 g ditridecylamine. The mixture was refluxed for 3.5 hours with removal of water. The volatile solvents were removed by heating under vacuum at 160° C. The product was filtered at 100° C. The brown liquid product had a molybdenum content of 5.0 percent.

EXAMPLE IV

A reactor was charged with 123 g (0.143 moles) of tallow and 26.6 g (0.258 moles) of diethanolamine. The reaction mixture was heated with stirring under nitrogen for 4 hours at 135°–140° C. Thereafter, a solution of 3.5 g ammonium heptamolybdate in 10 g water was added and heated to 120° C. with removal of water. Residual water was removed under vacuum. The liquid was filtered at 100° C. The amber liquid product had a molybdenum content of 1.1 percent.

EXAMPLE V

A molybdenum complex of coconut oil and diethanolamine was prepared according to the method described in Example III, except the amount of molybdenum trioxide used was 24.5 g. The brown liquid product contained 6.0 percent molybdenum.

EXAMPLE VI

Friction Test

The molybdenum complexes of the invention were tested for friction reducing properties by a modified Falex ring and block test procedure. This test is believed to simulate the Five Car Fleet Test on laboratory scale.

The Falex machine was stabilized by a break-in run with a base oil (Sunvis ®21 manufactured by Sun Oil Company) for 1 hour at 150° C. under a load of 4.54 kg and for 5 minutes at 114° C. followed by heating at 150° C.

After the break-in period, 100 ml base oil was added and the friction was measured as pound friction force at one minute intervals for 15 minutes at 108° C., 800 rpm and load of 2.27 kg. After draining the base oil and cleaning, the same ring and block was used for testing the sample. The values of pound friction force were converted to coefficient of friction which is defined as a ratio of friction force to applied force and compiled in Table I herein. The results indicate that the molybdenum complex of the invention described in Example I and used in this test substantially reduces the coefficient of friction of engine oils.

TABLE I

| | Falex Friction Test | | | |
|---|---|---|---|---|
| | Ingredient, Percent | | | |
| Sample | 1 | 2 | 3 | 4 |
| Base Oil | 100 | 99.9 | 99.75 | 99.5 |
| Molybdenum Complex | — | 0.1 | 0.25 | 0.5 |
| Coefficient Of Friction | | | | |
| At Start | 0.035 | 0.044 | 0.038 | 0.030 |
| After 1 minute | 0.040 | 0.041 | 0.036 | 0.025 |
| 2 minutes | 0.044 | 0.036 | 0.032 | 0.020 |
| 3 minutes | 0.045 | 0.033 | 0.030 | 0.016 |
| 4 minutes | 0.046 | 0.031 | 0.029 | 0.013 |
| 5 minutes | 0.047 | 0.029 | 0.027 | 0.011 |
| 6 minutes | 0.047 | 0.027 | 0.025 | 0.010 |
| 7 minutes | 0.047 | 0.026 | 0.023 | 0.010 |
| 8 minutes | 0.048 | 0.025 | 0.022 | 0.010 |
| 9 minutes | 0.048 | 0.025 | 0.021 | 0.008 |
| 10 minutes | 0.048 | 0.024 | 0.019 | 0.007 |
| 11 minutes | 0.049 | 0.024 | 0.018 | 0.007 |
| 12 minutes | 0.049 | 0.023 | 0.017 | 0.007 |
| 13 minutes | 0.049 | 0.023 | 0.016 | 0.007 |
| 14 minutes | 0.049 | 0.023 | 0.015 | 0.007 |
| 15 minutes | 0.049 | 0.023 | 0.015 | 0.007 |

EXAMPLE VII

Shell Four Ball Wear Test

The molybdenum complexes described in Example IV and Example I were evaluated as antiwear agents by the Shell Four Ball Wear Test. The test was conducted essentially according to the method described in ASTM D2266 procedure. Four slightly polished steel balls 12.5 mm in diameter were placed in a test cup and submerged in the test sample. The test oil was Sunvis 21. The test was carried out at a rotation speed of 1800 rpm under a load of 20 kg at 54.4° C. and 40 kg at 93° C. for 60 minutes. The diameter of wear scar produced by the samples containing additives and no additive was measured and compiled in Table II herein. The data indicate that the present additives have good antiwear properties at higher molybdenum concentrations.

TABLE II

| | Four Ball Wear Test | | | |
|---|---|---|---|---|
| | | | Scar Diameter, mm | |
| Sample | Active Ingredient | Percent | 20 kg | 40 kg |
| 5 | — | — | 0.76 | 2.0 |
| 6 | Molybdenum complex (Mo 6.0%) | 0.25 | 0.33 | — |
| 7 | Molybdenum complex (Mo 6.0%) | 0.50 | 0.30 | 0.45 |
| 8 | Molybdenum complex (Mo 1.0%) | 0.25 | 0.36 | — |

TABLE II-continued

| | | Four Ball Wear Test | | |
|---|---|---|---|---|
| | | | Scar Diameter, mm | |
| Sample | Active Ingredient | Percent | 20 kg | 40 kg |
| 9 | Molybdenum complex (Mo 1.0%) | 0.50 | 0.31 | — |
| 10 | Molybdenum complex (Mo 1.0%) | 2.00 | — | 0.50 |

The above embodiments have shown various aspects of the present invention. Other variations will be evident to those skilled in the art and such modifications are intended to be within the scope of the invention as defined by the appended claims.

What is claimed is:

1. An organic molybdenum complex prepared by reacting (a) about 1.0 mole of fatty oil having 12 or more carbon atoms, (b) about 1.0 to 2.5 moles diethanolamine and (c) a molybdenum source sufficient to yield about 0.1 to 6.0 percent of molybdenum based on the weight of the complex, the reaction being carried out at about 70° to 160° C.

2. An organic molybdenum complex according to claim 1 wherein the fatty oil is coconut oil and the molybdenum content is 1.0 to 1.25 percent based on the weight of the complex.

3. A lubricating composition comprising a major amount of a lubricating oil and about 0.01 to 5.0 percent of an organic molybdenum complex prepared by reacting (a) about 1.0 mole of fatty oil having 12 or more carbon atoms, (b) about 1.0 to 2.5 moles diethanolamine and (c) a molybdenum source sufficient to yield about 0.1 to 6.0 percent molybdenum based on the weight of the complex, the reaction being carried out at about 70° to 160° C.

4. A method of reducing fuel consumption in an internal combustion engine which comprises lubricating said engine with a lubricating composition comprising a major amount of a lubricating oil and about 0.01 to 5.0 percent of an organic molybdenum complex prepared by reacting (a) about 1.0 mole of fatty oil having 12 or more carbon atoms, (b) about 1.0 to 2.5 moles diethanolamine and (c) a molybdenum source sufficient to yield about 0.1 to 6.0 percent molybdenum based on the weight of the complex, the reaction being carried out at about 70° to 100° C.

* * * * *

UNITED STATES PATENT AND TRADEMARK OFFICE
CERTIFICATE OF CORRECTION

PATENT NO. : 4,889,647

DATED : Dec. 26, 1989

INVENTOR(S) : Eugene V. Rowan, Thomas J. Karol, Homer H. Farmer

It is certified that error appears in the above-identified patent and that said Letters Patent is hereby corrected as shown below:

Title page [57] Abstract, first line
"molbdenum" should be -- molybdenum --;

Column 2, line 8
"fatty oily" should be -- fatty oil --;

Column 2, lines 55-56
"napthenic" should be -- naphthenic --;

Column 3, lines 9-10
"heptamobybdate" should be -- heptamolybdate --.

Signed and Sealed this

Twenty-third Day of October, 1990

Attest:

HARRY F. MANBECK, JR.

*Attesting Officer*     *Commissioner of Patents and Trademarks*